United States Patent [19]

Georghiou

[11] Patent Number: 5,750,577
[45] Date of Patent: May 12, 1998

[54] CHROMOTROPIC ACID-FORMALDEHYDE AND 1-NAPHTHOL-FORMALDEHYDE POLYMERIC COMPOUNDS

[75] Inventor: Paris Georghiou, Newfoundland, Canada

[73] Assignee: Seabright Corporation Limited, Canada

[21] Appl. No.: 760,847

[22] Filed: Dec. 5, 1996

Related U.S. Application Data

[63] Continuation of Ser. No. 234,816, Apr. 28, 1994, abandoned.
[51] Int. Cl.[6] .................... A61K 31/05; A61K 31/255; A61K 31/22; A61K 31/235
[52] U.S. Cl. .................... 514/232; 514/510; 514/517; 514/518; 514/577; 514/709; 558/24; 558/46; 560/107; 560/108; 560/139; 562/36; 562/76; 562/89; 568/28; 568/33; 568/34; 568/39
[58] Field of Search .................... 514/510, 577, 514/709, 732, 517, 518; 560/107, 108, 139; 562/76, 89, 36; 568/33, 34, 39, 28; 558/24, 46

[56] References Cited

U.S. PATENT DOCUMENTS

| | | | |
|---|---|---|---|
| 4,980,354 | 12/1990 | Cairns et al. | 514/255 |
| 5,134,161 | 7/1992 | Venuti et al. | 514/481 |
| 5,166,173 | 11/1992 | Venuti et al. | 514/481 |
| 5,177,112 | 1/1993 | Horn | 514/654 |
| 5,196,452 | 3/1993 | Hwang | 514/577 |
| 5,242,946 | 9/1993 | Guindon | 514/510 |
| 5,441,983 | 8/1995 | Hwang | 514/562 |

OTHER PUBLICATIONS

Georghiu, Paris E., *Calix[4]naphthalines: Cyclic Tetramers of 1-Naphthol and Formaldehyde*, Tetrahedron Letters, vol. 34, No. 18, 1993, pp. 2887-2890.

Georghiu, Paris E., et al., *Synthesis of Calix[4]naphthalenes Derived from 1-Naphthol*, Journal of Organic Chemistry, vol. 60, No. 22, 1995., pp. 7284-7289.

Andreetti, Giovanni, et al., *Dissymmetric Calix[4]arenes with $C_4$-and $C_2$Symmetry, Synthesis, X-ray Structures, Conformational Fixation, and $^1H$ NMR Spectroscopic Studies*, Journal of Organic Chemistry, vol. 58, No. 15, 1993, pp. 4023–4032.

Czech, Bronislaw, et al., *Cesium Fluoride Assisted Synthesis of Macrocyclic Polyethers with Aromatic Subunits*, Journal of Heterocyclic Chemistry, Sep.–Oct. 1985, pp. 1297–1300.

Kitamura, et al., *Photo–Induced Dimerization of 1–Naphthoxide Anion*, Tetrahedron Letters, pp. 3261-3267, 1978.

Georghiou, Paris E., et al., *Synthesis of Dihomocalix[4] naphthalenes: First Members of a New Class of [1.2.1.2] (1,3)Naphthalenophanes*, Journal of Organic Chemistry, vol. 61, No. 11, 1996, pp. 3865–3869.

Georghiou et al., Calix[4]Naphthalenes: Cyclic Tetramers of 1–Naphthol and Formaldehyde, Tetrahedron Letters, 34(18): 287–2890 1993.

Georghiou, et al., Chemistry of Chromotropic Acid, etc., Can J. Chem. 69: 1207–1211 1991.

Georghiou et al., The Chemistry of the Chromotropic Acid Method, etc., Can J. Chem. 67: 871–876 1989.

Mohan et al., Sulfonic Acid Polymers, etc., Antiviral Research 18: 139–150 1992.

*Primary Examiner*—Peter O'Sullivan
*Attorney, Agent, or Firm*—Eckert Seamans Cherin & Mellott

[57] ABSTRACT

Novel medicinally-useful compounds are provided herein. These compounds include isomeric cyclic tetramers of formaldehyde and 1-naphthol, and the derivatives or analogues of such cyclic tetramers, and linear oligomers of chromotropic acid, or its derivatives or analogues with naphthalene.

12 Claims, No Drawings

CHROMOTROPIC ACID-FORMALDEHYDE AND 1-NAPHTHOL-FORMALDEHYDE POLYMERIC COMPOUNDS

RELATED APPLICATION

This application is a continuation of application Ser. No. 08/234,816, filed Apr. 28, 1994, now abandoned.

BACKGROUND OF THE INVENTION

1. Field of the Invention

This invention relates to the use of a novel class of cyclic formaldehydenaphthalene tetrameric compounds that are analogous to the well-known class of compounds known as "calixarenes", hereinafter referred to as "calixnaphthalenes".

2. Background of the Invention

The calixarenes described above are a subject of intense global research activity because of their important industrial and medicinal applications. The challenge in developing an effective therapy and prophylaxis for viral disease is to achieve inhibition of viral processes without producing extreme side effects and preferably without inducing viral resistance. Since viral replication requires use of the cellular apparatus of the host, treating virus infection by inhibiting viral replication can be lethal to the infected host cells as well. Ideally, the virus should be destroyed or made inactive in the host prior to its invasion of host cells. This is normally accomplished, with varying degrees of success, by the host's immune system, but this mechanism requires an earlier immune response, either by a prior infection or by vaccination. Furthermore, many viruses, e.g., Herpes Simplex viruses (HSV) are able effectively to elude a host's immune systems, and at least one virus, the human immunodeficiency virus (HIV) is known to cripple the host's immune system. Currently, the most widely used anti-viral agents are nucleosidic analogs. This class of drugs acts by disrupting viral replication either by producing enzymes required for nucleic acid processing, or by producing a defective viral genome, e.g., by premature termination of replication. As an example, acyclovir, a purine analog used in treating a variety of viral diseases, including herpes simplex virus-1 (HSV-1) and herpes simplex virus-2 (HSV-2), inhibits viral replication at several key points, including inhibition of viral thymidine kinase and DNA polymerase, and DNA strand elongation. Ribavirin, another purine analog, is the drug of choice in treating respiratory syncytial virus (RSV) infections. This compound appears to act by reducing cellular GTP levels, blocking the action of several GTP-dependent viral processes. To date, the most common drug treatment of HIV infection is with zidovudin (Azidothymidine; AZT), a thymidine analog which is particularly effective against human retroviruses. AZT acts with high affinity to block viral RNA-dependent DNA polymerase (reverse transcriptase), but does also block human DNA-polymerase and causes chain termination.

Other nucleic acid analogs include ganciclovir, vidarabine, idoxuridine, trifluridine and foscarnet (an inorganic phosphate analog). As indicated above, all of these drugs, by blocking viral replication, also have the capacity to disrupt normal host replication and/or DNA transcription processes as well.

Understanding the mechanisms of infection and replication of viruses has lead to alternate drug therapies, including attempts to block viral entry into cells, alter protein synthesis at the host ribosomes, complexation of viral DNA/RNA, and immunomodulation. Interferons are glycoproteins which have complex actions including enhancement of certain immune responses as well as direct antiviral action. They are more competent in preventing infection, rather than treating established viral infection, and their use leads to undesirable problems including acute, serious discomfort, bone narrow suppression, viral resistance, and development of host immune response to the interferon.

Treatment with "anti-sense" polymers of nucleic acids is a method in which the particular viral genome is the select target. The treatment provides a highly discriminating approach which would be expected to have minimal side-effects; its use as a therapeutic is hampered by problems of targeting, introduction into cells, and the quantity of material, that would be required to block each strand produced. Agents which bind to and interfere with host ribosomal protein synthesis will block viral replication. These include the toxin ricin, various plant proteins such as pokeweed anti-viral protein, alpha sarcin, and other low molecular weight compounds. The weakness with the use of these materials is their lack of selectivity. In the treatment of HIV, additional therapy has been developed by specifically targeting, for example, the unique retroviral enzyme, for example, reverse transcriptase. Non-retroviral systems do not produce or use this enzyme, but the virus cannot replicate without it.

In some instances, understanding of structural aspects of the mechanisms of replication of viruses has provided additional drug therapies. Certain viruses, including orthomyxovirus and paramyxovirus, herpes viruses, togaviruses and retroviruses, contain a viral envelope which surrounds the viral capsid and nucleic acid. During cell infection by an enveloped virus, the plasma membrane of the host cell is altered to include some viral-coded proteins and, as the viral nucleoprotein core exits the host cell in which it was assembled, it becomes enveloped with the modified membrane, thus forming the viral envelope. Because this structure is unique to host cells when they are virally infectious and distinct from normal cells, it can serve as an additional target for therapeutic assault.

Herpes simplex virus-1 (HSV-1) and herpes simplex virus-2 (HSV-2) are present as either lytic or latent herpes viruses, and are the causative agents in cold sores (HSV-1) and genital herpes, typically associated with lesions in the region of the eyes, mouth, and genitals (HSV-2). Both HSV-1 and HSV-2 viral infections are recurrent which can be activated in the form of lesions by a variety of stimuli.

Herpes infection can be treated with acyclovir, an acyclic nucleoside. The drug usually works in primary viral infection to limit the severity of infection. However, viral infection often recurs after drug treatment is stopped, and resistance to the drug may limit its usefulness over an extended treatment period.

Acquired immunodeficiency syndrome (AIDS) is caused by a pathogenic human retrovirus, human immunodeficiency virus (HIV), and still remains a formidable challenge to antiviral chemotherapy. Several compounds have been found to interact with specific events within the viral replicative cycle and yield promise as potential anti-AIDS drugs including the anti-HIV activity of a variety of naphthalene-disulfonic acids.

It has been taught, in a paper by P. Mohan et al, an Antiviral Research, 18(1992), 139–150, that four sulfonic acid polymers; [poly(4-styrenesulfonic acid)(PSS); poly (anetholesulfonic acid)(PAS); poly(vinylsulfonic acid)(PVS); and poly(2-acrylamido-2-methyl-1-propanesulfonic acid)(PAMPS)] have been found to inhibit the cytopathicity of HIV-1 and HIV-2 in MT-4 cells at concentrations that are not toxic to the host cells. The sulfonic acid polymers were also found to inhibit syncytium formation in co-cultures of MOLT-4 cells with HIV-1- or HIV-2-infected HUT-78 cells. They were also found to inhibit binding of anti-gp120 mAb to HIV-1 gp 120 and to block adsorption of HIV-1 virions to MT-4 cells. PSS and PAS, but not PVS and PAMPS, were found to interfere with the binding of OKT4A/Leu3a to the CD4 receptor.

Many naphthalene compounds have been said to have medicinal properties. For example, U.S. Pat. No. 4,980,354 patented Dec. 25, 1990 by J. Cairns et al provided tetrahydronaphthalene and indene derivatives with the following general formula and their pharmaceutically acceptable salts:

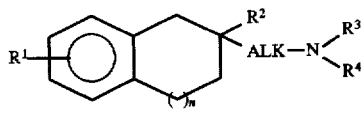

wherein the substituents $R^1$, $R^2$, $R^3$, $R^4$ and ALK had specially defined values, and wherein n had the value 0 or 1. Such compounds were said to be typical monoamine reuptake blockers with additional $\alpha_2$ antagonist activity and were said to have anti-depressant activity without being sedative. They were also said to be suitable for treating patients with anxiety disorders, e.g., panic disorders.

U.S. Pat. No. 5,134,161 patented Jul. 28, 1992 by M. C. Vesuti et al provided a teaching that psoriasis in mammals may be relieved by topically administering naphthalenes of the following general formula:

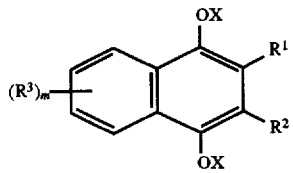

wherein: $R^1$, $R^2$, $R^3$, and X groups had specifically-defined values. Such compounds were said to be useful for the treatment of disease-states caused by lipoxygenase activity in mammals, particularly 5-lipoxygenase activity, when administered systemically.

U.S. Pat. No. 5,155,132 patented Oct. 13, 1992 by M. C. Vesuti et al taught that psoriasis in mammals could be relieved by topically administering naphthalenes of the following general formula:

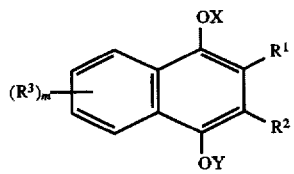

wherein: $R^1$, $R^2$, $R^3$, m, X and Y were as specifically-defined.

U.S. Pat. No. 5,166,173 patented Nov. 24, 1992 by K. M. Hwang provided a method of inhibiting cell infection by herpes simplex virus-1 or -2 by contacting the virus with a macrocyclic chromotropic acid compound, in an amount effective to inhibit cell infectivity of the virus. Such compound was one having the following general formula:

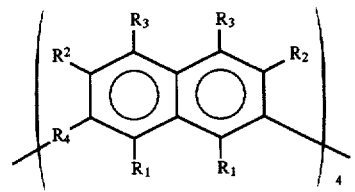

wherein $R_1$, $R_2$, $R_3$ and $R_4$ were as specifically-defined.

U.S. Pat. No. 5,177,112 patented Jun. 5, 1993 by A. S. Horn provided certain novel compounds having the following structural formula:

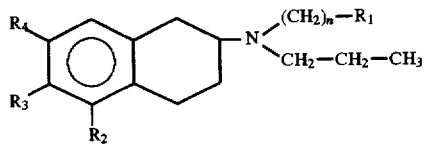

wherein $R_1$, $R_2$, $R_3$ and $R_4$ are as specifically-defined. Such compounds were said to be useful for inducing a dopaminergic response and reducing the intraocular pressure in a mammal.

U.S. Pat. No. 5,196,452 patented Mar. 23, 1993 by K. M. Hwang et al provided compounds and methods for inhibiting cells infected by an enveloped virus. The compounds were macrocyclic chromotropic acid derivatives which were composed of subunits of a chromotropic acid derivative linked between the 2 and 7 ring positions of adjacent subunits by methylene-linked bridges which could be substituted at a variety of naphthalene ring and bridge positions. Such compounds had the general formula:

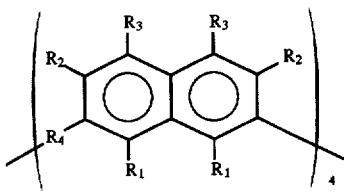

wherein $R_1$, $R_2$ and $R_3$ were as specifically-defined. The compounds were said to be administered parenterally, orally, or topically for treating infection by enveloped viruses.

U.S. Pat. No. 5,242,946 patented Sep. 7, 1993 by Y. Guindon provided a group of known naphthalene derivatives which were said to be useful for preventing or relieving herpes viral infections. Such compounds were naphthalene derivatives of the following general formula:

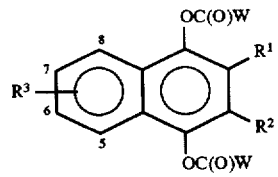

wherein: $R^1$, $R^2$, and $R^3$ and W were as specifically recited, and n was 0, 1 or 2.

A paper by Paris E. Georghiou and Chi Keung (Jimmy) Ho entitled "The Chemistry of the Chromotropic Acid Method for the Analysis of Formaldehyde", published in Can. J. Chem. 67, 871(1989), described the chemistry of the reaction between chromotropic acid (CTA) and formaldehyde.

In that paper it was theorized that the reaction scheme was as follows:
Thus it was suggested that a monosubstituted chromotropic acid-formaldehyde adduct was likely being formed in the
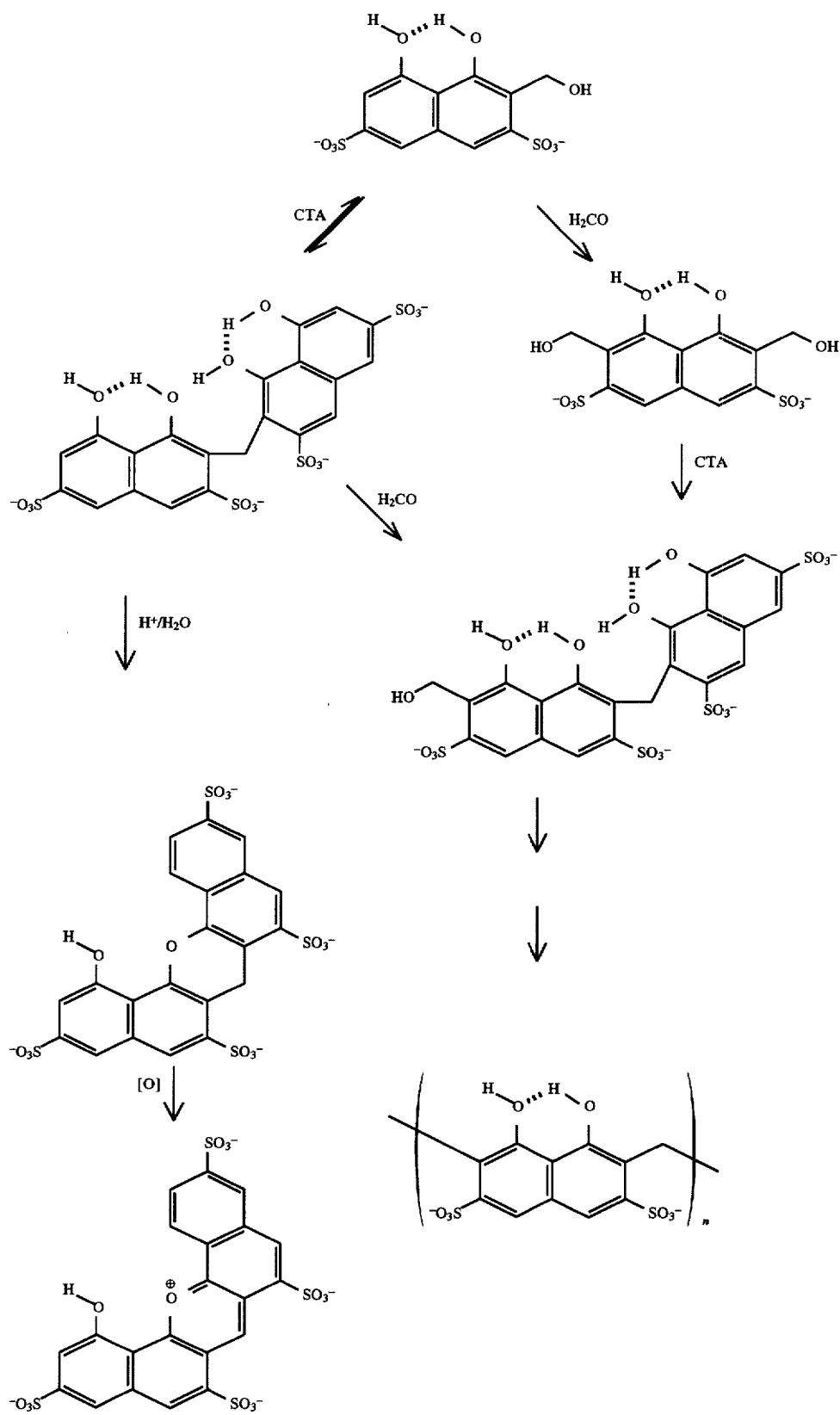

earlier stages of the reaction. Subsequently, the adduct was being converted in the presence of excess formaldehyde into the disubstituted ortho-ortho linear polymer or other intermediate adducts as outlined above.

The authors concluded that the site of the reaction of formaldehyde with chromotropic acid in aqueous or aqueous acidic conditions most likely occurred on the carbon atom which was ortho- to both the hydroxyl and sulphonic acid groups. An adduct containing a methylene bridge formed by the coupling of a single molecule of formaldehyde between two molecules of chromotropic acid could be isolated and characterized by $^1$H and $^{13}$C NMR spectroscopy.

Another paper by Paris E. Georghiou, Chi Keung (Jimmy) Ho, and Chester R. Jablonski, Can. J., Chem. 69, 1207 (1991), entitled "Chemistry of Chromotropic Acid. $^1$H and $^{13}$C NMR Spectroscopy of Chromotropic Acid and Its Derivatives", described the spectra of chromotropic acid and some of its derivatives.

SUMMARY OF THE INVENTION

1. Aims of the Invention

The utility of these compounds was not disclosed in these papers. However, the three above-noted U.S. Pat. Nos. 5,166,173; 5,242,946 and 5,441,983 described the anti-viral activity of very closely related formaldehyde-chromotropic acid (CTA) tetrameric compounds. These cyclic tetrameric formaldehyde-CTA compounds were said to show anti-HIV activity as well as anti-HSV and anti-RSV activity. However, it is one object of the present invention to provide non CTA analogues of such CTA tetrameric compounds which may have even more anti-viral activity.

It is therefore a general object of the invention to provide compounds which are effective in inhibiting cell infection by enveloped viruses.

It is another object of the invention to provide a method of inhibiting cell infection by enveloped viruses.

2. Statements of Invention

In addition to describing oligomers of formaldehyde and naphthalene, the present invention describes a class of isomeric cyclic tetramers of formaldehyde and 1-naphthol that are analogous to the calix[4]arenes and the calix[4] resorcinarenes. This invention is based on the published disclosure in Tetrahedron Letters, Vol. 34, No. 18, pp. 2887–2890, Apr. 27, 1993.

The present invention thus provides the following novel cyclic tetramers of formaldehyde and 1-naphthol, and the derivatives or analogues of such cyclic tetramers having the general structure represented by formulas 2–5:

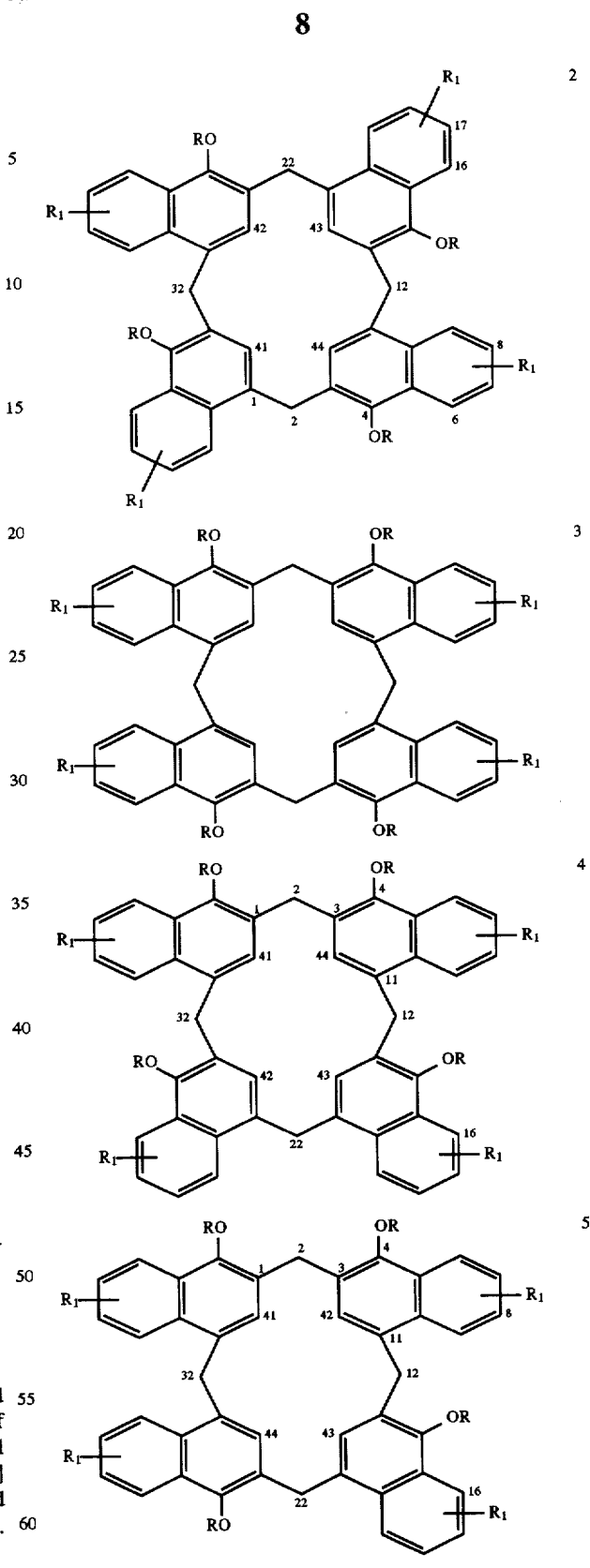

wherein: R=H, alkyl, aromatic, CO-alkyl, or CO-aromatic; and $R_1$=H, alkyl, aromatic, CO-alkyl, CO-aromatic, $SO_2R$ or $SO_3R$.

The present invention also provides a method for preventing or relieving cell death or damage due to viral infections in a mamal which comprises administering, to the mammal, an effective amount of a cyclic tetramer of formaldehyde and 1-naphthol, and the derivatives or analogues of such cyclic tetramer, having the general structure represented by formulas 2–5:

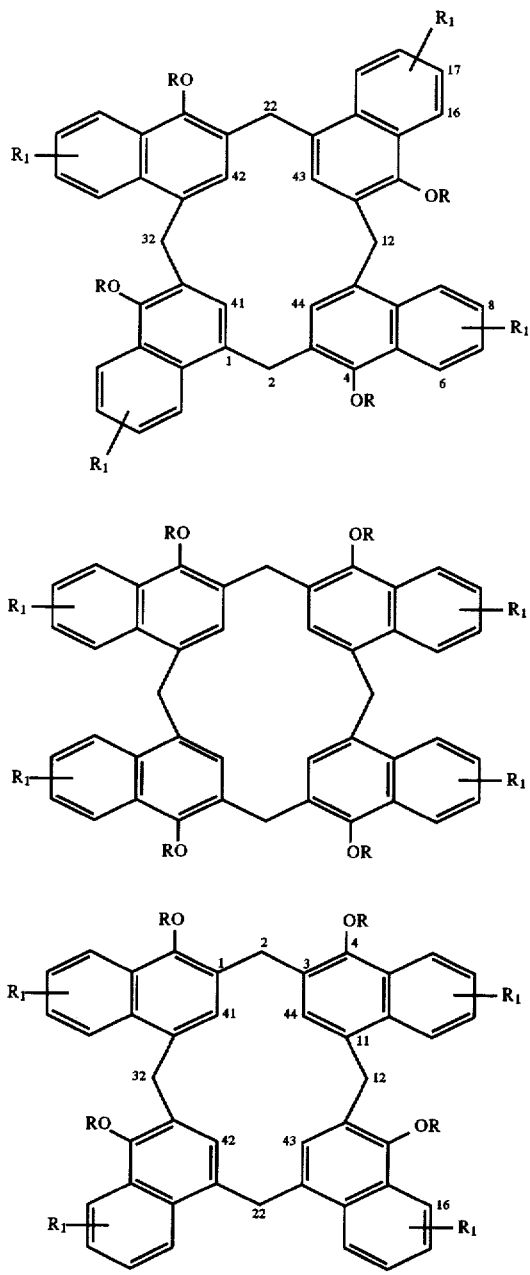

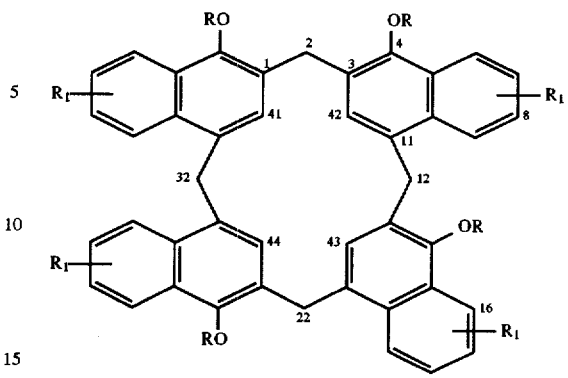

wherein: R=H, alkyl, aromatic, co-alkyl, or CO-aromatic; and $R_1$=H, alkyl, aromatic, CO-alkyl, CO-aromatic, $SO_2R$ or $SO_3R$.

3. Other Features of the Invention

By another feature, the present invention provides a method of inhibiting cell infection by an enveloped virus comprising administering to the site of infection a therapeutically effective dose of a macrocyclic tetramer of 1-naphthol or its derivatives or analogues with formaldehyde.

In one specific feature thereof, the macroscopic tetramer is of 1-naphthol or its derivatives or analogues with formaldehyde having the following structures 2–5: wherein: R=H, alkyl, aromatic, CO-alkyl, or CO-aromatic; and $R_1$=H, alkyl, aromatic, CO-alkyl, CO-aromatic, $SO_2R$ or $SO_3R$.

In another specific feature of the invention, a method is provided for inhibiting cell infection by an enveloped virus comprising administering to the site of the infection a therapeutically-effective dose of an oligomer of chromotropic acid, its derivatives or analogues with formaldehyde, having the formula:

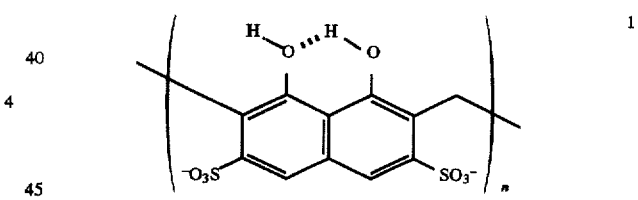

In variants of the above-described methods, the enveloped virus is selected from the virus families Orthomyxovirus, Paramyxovirus, Retrovirus and Herpesvirus; or is selected from the group consisting of HSV-1, HSV-2, Human Immunodeficiency virus (HIV), Influenza A, Influenza B, and Respiratory Syncytial Virus (RSV).

4. Generalized Description

In the present specification and claims the term "alkyl" includes alkyl groups containing one to seven or even more carbon atoms including straight chain groups, or branched chain groups. Illustrative of such groups are, for example, methyl, ethyl, n-propyl, i-propyl, s-butyl, 2,2- dimethylpropyl, n-hexyl, 2-methylpentyl, n-heptyl, 2,2-dimethylbutyl and 3,3-dimethylpentyl.

The term "phenyl-lower-alkyl" includes an optionally substituted phenyl ring attached to an alkylene chain of one to six or even more carbon atoms.

In the present specification and claims, the term "CO-alkyl" includes an alkoxyl group, i.e., a straight or branched chain aliphatic group of one to six or even more carbon atoms having an oxygen moiety bonded thereto. Examples include methoxy, ethoxy, n-propoxy, i-propoxy, n-butoxy, i-butoxy, s-butoxy, t-butoxy and n-pentyloxy.

As used in the present specification and claims the term "aromatic" includes benzene, toluene, o-xylene, m-xylene, p-xylene, hemimellitene, pseudocumene, mesitylene, prehnitene, isodurene, pentamethylbenzene, hexamethylbenzene, ethylbenzene, n-propylbenzene, cumene, n-butylbenzene, t-butylbenzene, p-cymene, 1,3,5-triethylbenzene, 1,2,3-trimethylbenzene, 1,2,4-trimethylbenzene, hexaethylbenzene, styrene, allylbenzene, stilbene (trans), diphenylmethane, triphenylmethane, tetraphenylmethane, diphenyl, p-terphenyl, p-quaterphenyl, 1,3,5,-triphenylbenzene, naphthalene, antracene, phenanthrene, 1,2,3,5tetramethylbenzene, 1,2,3,4-tetramethylbenzene, 1,2,4,5-tetramethylbenzene, 1,2,3,4,5-pentamethylbenzene, hexamethylbenzene, 1-methylnaphthalene, 2-methylnaphthalene, 1-methylanthracene, and 2-methylanthracene.

As used in the present specification the term "CO-aromatic" includes an aromatic ring as above described, which is attached to an alkylene chain of one to six or even more carbon atoms having an oxygen atom bonded thereto. Examples include benzyloxy, 4-chlorophenylethoxy, phenyl-n-proxy and 2-methoxyphenyl-n-hexyloxy.

"Pharmaceutical acceptable salts" as used herein include acid addition salts derived from acids, e.g., hydrochloric acid, sulphuric acid, phosphoric acid, acetic acid, propionic acid, glycolic acid, maleic acid, fumaric acid, malonic acid, succinic acid, tartaric acid, lactic acid, citric acid, ascorbic acid, salicylic acid, benzoic acid, methanesulphonic acid, obtained by reaction of the free base of the compounds of this invention with an appropriate acid in a suitable solvent.

The complexity of the reaction of 1-naphthol with formaldehyde is well-known and it has been assumed that cross-linked polymers are formed. By way of contrast, the reaction of 2-naphthol with formaldehyde under either base catalysis or acid catalysis readily affords a single product, bis-(2-hydroxy-1-naphthyl)-methane. It has now been discovered that the base-catalyzed condensation of 1-naphthol with formaldehyde yields three isomeric cyclic tetramers. These are novel members of the class of naphtholformaldehyde oligomers and are hereby referred to as "calix[4]naphthalenes", named by analogy with the wellknown calix[n]arenes and calix[n]resorcinarenes.

Fractional crystallization of the crude product mixture obtained from the reaction in DMF of 1-naphthol, formaldehyde and potassium carbonate affords four products whose mass spectra indicate them to be isomeric tetramers, each having a molecular ion peak at m/s=624. The four cyclic tetrameric isomers that are possible are depicted as 2–5 above.

The first product that can be isolated from the reaction mixture crystallizes from acetone to yield a compound, (structure 2 below), whose $^{13}C$ NMR spectrum shows twelve signals.

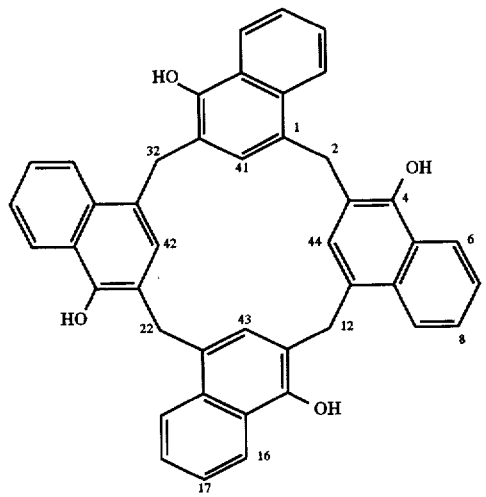

By symmetry considerations, 2 has $C_4$ symmetry and thus should exhibit only eleven $^{13}C$ NMR signals. APT-$^{13}C$ NMR however reveals that the two highest-field signals at δ 31.9 and 30.7 are respectively due to a methylene and a methyl carbon. The carbonyl carbon signal of acetone is normally of much lower intensity than the methyl signal and is not evident in the $^{13}C$ NMR spectra of our product. The $^{13}C$ NMR (see Table 1 hereinafter), $^1H$ NMR, HETCOR, NOED spectra, and MS data are all consistent for structure 2 (above) which contains acetone as a possible inclusion molecule. In the $^1H$ NMR spectrum the methylene protons appear as a singlet at δ 4.29 at ambient temperature, indicating conformational flexibility.

The second compound that can be isolated crystallizes from ethyl acetate (structure 4 below), its $^{13}C$ NMR spectrum reveals only twenty-one clearly resolved signals but its APT-$^{13}C$ spectrum shows that a pair of quaternary carbon signals and a pair of aromatic methane signals overlap.

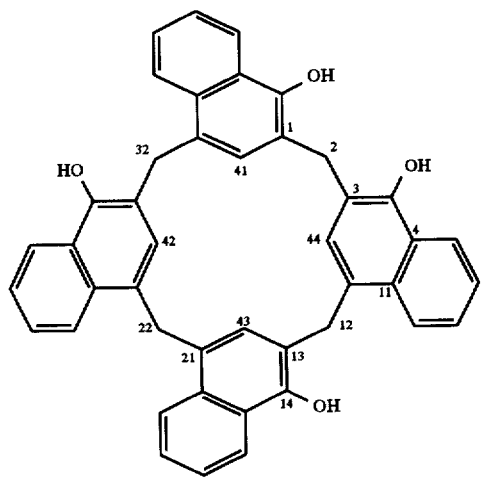

In addition, the height of one of the aliphatic methylene carbon signals is double that of each of the other two, confirming the presence of twenty-three carbon signals which is to be predicted for 4. $^1H$ NMR, HETCOR, NOED spectra and MS data are also consistent for structure 4 which has $C_2$ symmetry. In its $^1H$ NMR spectrum the methylene protons appear as three singlets at δ 4.08, 4.29 and 4.40 having relative intensities of 1,2:1. This isomer is thus conformationally flexible. The third isomer, which is the most difficult to isolate, crystallizes from diethyl ether (structure 5 below).

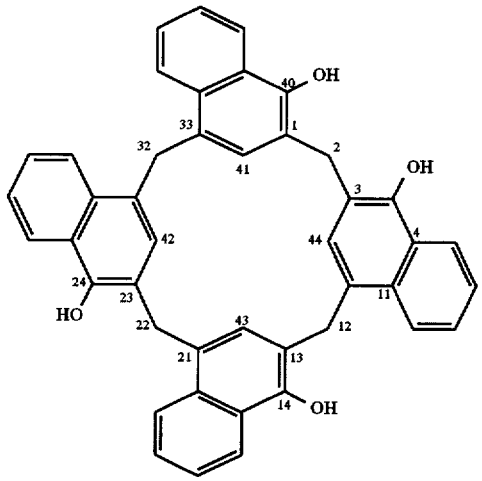

Its $^{13}$C NMR spectrum shows only forty-two clearly resolved signals, with some obvious overlapping in a group of methine aromatic carbon signal which are centered around δ 124.5 in the $^1$H NMR spectra the methylene protons appear as signals of equal intensities at δ 4.09, 4.21, 4.32 and 4.45.

$^1$H NMR, HETCOR, NOED spectra and MS data are also consistent for this compound, (structure 5 below), which does not possess any symmetry.

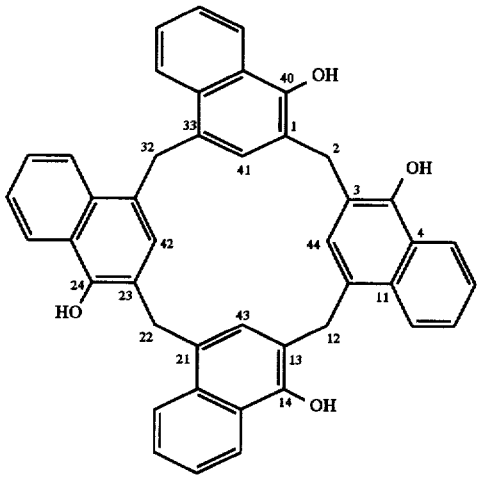

This isomer (compound 5) is also conformationally flexible at ambient temperatures.

The $^1$H NMR spectra of the crude reaction product reveal that structures 2, 4, and 5 are the major components of the mixture. A ratio of 1.0:2.2:3.0 for structure 2; structure 4; and structure 5 can be estimated from the integration of the intra-annular aromatic protons at C41–C44 that are observed in the $^1$H NMR spectra of the crude reaction produced.

In particular, four naphthalene rings can be linked to one another at several different positions by CH$_2$ bridges. This could result in the formation of structural isomers whose "lower rim" is either of the same size, as in the case of the examples reported herein (16-membered carbocycle), or are of different sizes (12–28-membered carbocycle). Based on the naming and numbering system used for the calix[4] naphthalenes, compounds 2, 4 and 5 could be named as 4,14,24,34-tetrahydroxycalix[4]-naphthalene, 4,14,30,40- tetrahydroxycalix[4]naphthalene, and 4,14,24,40- tetrahydroxycalix|4|naphthalene, respectively.

DETAILED DESCRIPTION OF THE PREFERRED EMBODIMENTS

1. Examples of the Invention
Preparation of Compounds 2, 4 and 5.

To a solution of 1.44 g of purified 1-naphthol in 10 ml of DMF were added 0.70 ml of formalin solution (37%) and 1.0 ml of aqueous 10% potassium carbonate. The mixture was refluxed under nitrogen for 30 h and then cooled to 5° C. overnight. The precipitate was filtered, washed with deionized water until the washings were neutral to pH paper, and dried under vacuum overnight. Crystallization from acetone gave 0.15 g (9.6%) of compound of structure 2 as a colourless powder, mp>300° C. (with decomposition). $^1$H NMR (DMSO), δ 4.29 (s, H-2, H-12, H-22, H-32), 6.62 (s, H-41, H-42, H-43, H-44), 7.53 (m, H-7, H-8, H-17, H-18, H-27, H-28, H-37, H-38), 8.02 (m, H-9, H-19, H-29, H-39), 8.19 (m, H-6, H-16, H-26, H-36). $^{13}$C (DMSO) for selected assignments see Table 1; δ 30.7 (acetone), 31.9, 119.9, 122.6, 123.8, 124.5, 125.2, 125.8, 128.0, 128.6, 131.5, 147.9; IR(KBr):3404 cm$^{-1}$; MS m/z:624 (M$^+$, 52%). The mother liquor from the first filtration was poured onto a mixture of 5 g of ice and 10 ml of 5% aqueous HCl with stirring. The precipitate was filtered, washed with water until the washings were neutral to pH paper, and dried under vacuum. Crystallization from ethyl acetate gave 0.25 g (16%) of 4 as a colourless powder, mp>300° C. (With decomposition). $^1$H NMR (DMSO); δ 4.08 (s, H-22), 4.29 (s, H-12, H-32), 4.40 (s, H-2), 6.72 (s, H-41, H-44), 6.83 (s, H-43, H-43), 7.40 (m, H-7, H-8, H-16, H-18, H-26, H-27, H-36, H-37), 7.78 (d, H-9, H-35), 8.08 (m, H-19, H-25), 8.18 (m H-16, H-28), 8.31 (d, H-6, H-38); $^{13}$C (DMSO) for selected assignments see Table 1. δ 31.6, 313.6, 36.7, 120.3, 120.9, 122.2, 122.2, 122.8, 123.7, 123.9, 124.6, 124.8, 125.4, 125.4, 125.9, 127.6, 127.7, 128.5, 128.5, 128.7, 128.4, 131.2, 131.4, 147.31 147.8IR (KBr): 3404 cm$^{-1}$, MS m/z: 624 (M$^+$, 18%). The mother liquor from the ethyl acetate crystallization was evaporated to dryness. The residue was crystallized from diethyl ether to give 79 mg (5.0%) of 5 as a light yellow powder, mp>250° C. (with decomposition). $^1$H NMR (DMSO); δ 4.09 (s, H-2), 4.21 (s, H-22), 4.32 (s, H-12), 4.45 (s, H-32), 6.64 (s, H-44), 6.66 (s, H-41), 6.70 (s, H-42), 6.80 (s, H-43), 7.40 (m, H-7, H-8, H-17, H-18, H-27, H-28, H-36, H37), 7.79 (d, H-35), 7.97 (d, H-19), 7.98 (d, H-29), 8.08 (d, H-9), 8.18–8.22 (m, H-6, H-16, H-26, H-38). $^{13}$C (DMSO) for selected assignments see Table 1: δ 30.0, 31.6, 31.7, 33.2, 120.2, 120.4, 120.6, 120.9, 122.3, 122.4, 122.5, 122.8, 123.5, 123.6, 123.8, 124.0, 124.3, 124.4, 124.5(X3), 125.1, 125.2, 125.4, 125.5, 125.6, 125.7, 125.8, 127.5, 127.7, 127.9, 128.1, 128.2, 128.7, 129.1, 129.4, 131.1, 131.3, 131.4, 131.5, 147.7, 147.9, 148.0, IR (KBr): 3404 cm$^{-1}$; MS m/z: 624 (M$^+$, 39%).

TABLE 1

Selected $^{13}$C NMR Chemical Shifts for compounds 2, 4 and 5 in DMSO$_{d6}$ (δ$_{ppm}$) at 75 MHz. Assignments based upon $^{13}$C—APT; HETCOR and NOED spectra. Signals denoted * were not unambiguously assigned.

| 2 | | 4 | | 5 | |
|---|---|---|---|---|---|
| carbon | δ$_c$ | carbon | δ$_c$ | carbon | δ$_c$ |
| 2,12,22&32 | 31.9 | 12&32 | 31.6 | 32 | 30.0 |

TABLE 1-continued

Selected $^{13}$C NMR Chemical Shifts for compounds 2, 4 and 5 in DMSO$_{d6}$ ($\delta_{ppm}$) at 75 MHz. Assignments based upon $^{13}$C—APT; HETCOR and NOED spectra. Signals denoted * were not unambiguously assigned.

| 2 | | 4 | | 5 | |
|---|---|---|---|---|---|
|   |   | 22 | 33.6 | 12 | 31.6 |
|   |   | 2 | 36.7 | 22 | 31.7 |
|   |   |   |   | 2 | 33.2 |
| 3,13,23&33 | 119.9 | 1&3 | 120.3 | 1;3 | 120.2*;120.4* |
|   |   | 13&31 | 120.9 | 13;23 | 120.6*;120.9* |
| 41,42,43&44 | 128.6 | 41&44 | 128.5 | 41 | 128.2 |
|   |   | 42&43 | 129.4 | 43 | 128.7 |
|   |   |   |   | 42 | 129.1 |
|   |   |   |   | 44 | 129.4 |
| 1,11,21&31 | 131.5 | 21&23 | 131.2 | 11;21 | 131.1*;131.3* |
|   |   | 11&33 | 131.4 | 31;33 | 131.4*;131.5* |
| 4,14,24&34 | 147.9 | 14&30 | 147.3 | 4;14 | 147.6*;147.7* |
|   |   | 4&40 | 147.8 | 24;40 | 147.9*;148.0* |

OPERATION OF PREFERRED EMBODIMENTS

These compounds are believed to be effective as anti-viral agents in the same manner, but to a greater extent, than those described above in U.S. Pat. Nos. 5,196,452 and 5,166,173.

Thus the compounds of this invention are believed to inhibit cell infection by a variety of enveloped and non-enveloped viruses, e.g. enveloped viruses, for example the herpes viruses, herpes simplex virus-1 (HSV-1) and herpes simplex virus-2 (HSV-2), which are double-stranded DNA viruses; human immunodeficiency virus (HIV), an RNA retrovirus; and influenza A and B and respiratory syncytial viruses (RSV), all RNA viruses; and non-enveloped viruses, for example, adenovirus, a double-stranded DNA virus; and rhinovirus, a single-strand RNA virus, Typically, inhibition of virus infectivity may be measured by the extent of inhibition of cytopathic effects detectable in infected cultured cells. Inhibition of HSV-1 and HSV-2 infectivity in cultured cells may also be shown by inhibition of virus binding to infectable cells, and inhibition of viral yields in infected cells.

Toxicity in cell culture may be examined using a panel of human cell lines. In such examination, the selected macrocyclic compound of this invention may be added to cell cultures at a final concentration of 5, 10, 15, 50, or 100 µg/ml. Three days later the cells may be washed to remove drug, and stained with a vital stain, to detect dead (stained) cells.

The compounds of this invention may be tested for inhibition of cytopathic effects in cultured, HSV-infected cells. In such method, Vero cells may be infected with HSV-1 or HSV-2 and way be allowed to grow in culture until cytopathic effects are clearly visible. In the absence of infection, the cells would form an even monolayer of fibroblast-like cells. With HSV infection, a cytopathic effect characterized by round cells in suspension nay be clearly evident after 24 hours, followed by clumping and lysis of infected cells after 24-72 hours.

The compounds of this invention may further be tested for activity against HSV infection in a plaque reduction assay. In such assay, Vero cells, after overnight incubation, may be exposed to serial dilutions of the selected compounds of this invention, from 0.625-10 µg/ml, and HSV-1 or HSV-2 virus for two hours. After washing to remove drug and extracellular virus, the cells may be further incubated, then stained and counted for plaque formation. Percent inhibition may be determined by dividing plaques produced by total number of plaques in infected, untreated controls. From the dose response curve of plaques (expressed as percent of control), the dose required to produce 50% plaque reduction, $ED_{50}$, may be determined.

The ability of selected compounds of this invention to inhibit HSV-1 and HSV-2 viral yield at selected drug concentrations up to 10 µg/ml may be assessed in the viral inhibition assay. In such assay, cultured Hela cells may be exposed to serially diluted selected compounds of this invention and virus, allowed to grow for 24 hours, then freeze/thawed 3 times to release virus particles. Vero cells may be infected with serial dilutions of the viral lysates were assayed for plaque counts as described above. The drop in viral yield, as a function of drug concentration, may then be plotted.

The inhibitory effect of the compounds of this invention against drug-resistant strains of HSV-1 and HSV-2 may be compared with several anti-viral agents which have been used in treating HSV infection. Those prior art compounds which may be compared include the nucleoside analogues acyclovir (ACV), ganciclovir (DHPG), phosphonoformate (PFA), and phosphomethoxyethyladenine (PMEA). Inhibition of viral yield may be determined, as described above, by infecting Hela cells in the presence of wild type or drug-resistant strains of HSV-1 or HSV-2, and serial dilutions of a selected anti-viral compound, and infecting Vero cells with serial dilutions of the Hela cell lysate, as above.

The compounds of this invention may be tested for inhibition of cytopathic effects in cells infected with one of two HTLV-III strains, HTLV-III$_\beta$, and RF-II strains. In such testing, cells chronically infected with HTLV-III$_\beta$ or RF-II HIV strains may be incubated in the presence of serial dilutions of the selected compounds of the present invention, then further formation was scored under phase microscopy. The concentration effective to produce complete inhibition of syncytia formation $ED_{100}$, is determined.

The ability of compounds of this invention to inhibit cell infection by a rhinovirus and adenovirus 5 and 7 which are non-enveloped viruses, may also be studied. In such study, Verb cells ($10^5$) may be infected with a rhinovirus in the presence of the selected compounds of this invention, at concentrations ranging between 1-100 µg. Twenty-four hours after virus infection, the cells may be examined for cytopathic effect, evidencing viral infection.

Compounds according to this invention can be mixed with a suitable pharmaceutical carrier in order to obtain a pharmaceutical preparation for either oral, local or parenteral administration.

The preferred daily dose may be between 0.01 and 50 mg and for human use a daily dose between 5 and 500 mg is common. For the purpose of administration, the compound of this invention is processed in the form suitable for oral, local or parenteral administration, for example as a tablet, pill capsule, solution, emulsion, paste or spray. The dosage which may be administered is a pharmaceutically effective dose, defined as a dose effective to inhibit viral infection of host cells. It is believed that doses of the compounds of this invention in the range 1-50 µg/ml should be generally effective in inhibiting viral infection of cells. Thus, for many applications, an effective dose would be one which produces a concentration of compound of this invention in this range at the site of infection. For topical administration, a composition containing between 1-5% or more of the compound of this invention is suitable.

In general, a pharmacologically-effective daily dose can be from 0.01 mg/kg to 100 mg/kg per day, bearing in mind, of course, that in selecting the appropriate dosage in any specific case, consideration must be given to the patient's weight, general health, metabolism, age and other factors which influence response to the drug.

The compounds of this invention used in the method of this invention may be administered topically, for example, in the treatment of herpes virus infection. Alternatively, the compounds of this invention may be administered orally or parenterally, for delivery of the compounds of this invention to the bloodstream. In another embodiment, the macrocyclic compound of this invention may be administered intranasally, or by direct application to mucosal tissue, or by inhalation for uptake by the lungs.

The term "treatment" as used herein covers any treatment of a disease in a mammal, particularly a human, and includes: (i) preventing the disease from occurring in a subject which may be predisposed to the disease but has not yet been diagnosed as having it; (ii) inhibiting the disease, i.e. arresting its development; or (iii) relieving the disease, i.e., causing regression of the disease.

The compounds of this invention may be formulated with suitable pharmaceutical vehicles known in the art to form particularly effective topical compositions. An effective amount of the compounds of this invention is about 0.001% w to about 10% w of the total formulated composition. The rest of the formulated composition usually consists of about 90% w to about 99.999% w of a suitable excipient which may include a pharmaceutically-acceptable solvent and other pharmaceutically-acceptable additives to form a topically effective pharmaceutical formulation.

A pharmaceutically-acceptable solvent is one which is substantially non-toxic and non-irritating under the conditions used and may be readily formulated into any of the classical drug formulations such as powders, creams, ointments, lotions, gels, foams, aerosols, solutions and the like. Particularly suitable solvents include water, ethanol, acetone, glycerine, propylene carbonate, dimethylsulfoxide (DMSO), and glycols, e.g., 1,2-propylene diol, i.e., propylene glycol, 1,3-propylene diol, polyethylene glycol having a molecular weight of from 100 to 10,000, dipropylene glycol, etc. and mixtures of the aforementioned solvents with each other.

A topical cream may be prepared as a semi-solid emulsion of oil in water or water in oil. A cream base formulation by definition is an emulsion, which is a two phase system with one liquid (for example fats or oils) being dispersed as small globules in another substance (e.g., a glycol-water solvent phase) which may be employed as the primary solvent for the naphthalenes therein. The cream formulation may contain fatty alcohols, surfactants, mineral oil or petrolatum and other typical pharmaceutical adjuvants, e.g., anti-oxidants, antiseptics, or compatible adjuvants.

The compounds of this invention may also be formulated as topical ointments. A "classical" ointment is a semisolid anhydrous composition which may contain mineral oil, white petrolatum, a suitable solvent, e.g., a glycol and may include propylene carbonate and other pharmaceutically suitable additives, e.g., surfactants, for example SPAN™ and TWEEN™, or wool fat (lanoline), along with stabilizers, e.g., antioxidants and other adjuvants as mentioned before.

For oral administration, a pharmaceutically-acceptable non-toxic composition is formed by the incorporation of any of the normally employed excipients, e.g., pharmaceutical grades of mannitol, lactose, starch, magnesium stearate, sodium saccharin, talcum, cellulose, glucose, sucrose, magnesium, carbonate, and the like. Such compositions take the form of solutions, suspensions, tablets, pills, capsules, powders, sustained release formulations and the like. Such compositions may contain about 2%–95% active ingredient.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents and the like, such as for example, sodium acetate, sorbitan monolaurate, triethanolamine oleate, etc.

For systemic administration via suppository, traditional binders and carriers include, e.g., polyalkalene glycols or triglycerides.

The pharmaceutical composition may be in a form suitable for oral use, for example, as tablets, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents, and preserving agents in order to provide a pharmaceutically elegant and palatable preparation. Tablets contain the active ingredient in admixture with non-toxic pharmaceutically-acceptable excipients which are suitable for manufacture of tablets. These excipients may be, for example, inert diluents, for example calcium carbonate, sodium carbonate, lactose, calcium phosphate, or sodium phosphate; granulating and disintegrating agents, for example maize starch, or alginic acid; binding agent, for example starch, gelatine, or acacia; and lubricating agents, for example magnesium stearate, stearic acids, or talc. The tablets may be uncoated or they may be coated by known techniques to delay disintegration and adsorption in the gastrointestinal tract and thereby provide a sustained action over a longer period.

Formulations for oral use may also be presented as hard gelatine capsules wherein the active ingredient is mixed with an inert solid diluent, for example calcium carbonate, calcium phosphate, or kaolin, or as soft gelatine capsules wherein the active ingredient is mixed with an oil medium, for example, arachis oil, liquid paraffin, or olive oil.

Aqueous suspensions may contain the active macrocyclic compound of this invention in admixture with excipients suitable for the manufacture of aqueous suspensions. Such excipients include suspending agents, for example, sodium carboxymethylcellulose, methylcellulose, hydroxypropylmethylcellulose, sodium alginate, polyvinylpyrrolidone, gum tragacanth, and gum acacia; dispersing agents may be a naturally-occurring phosphatide, for example lecithin, or condensation products of an alkylene oxide with fatty acids, for example of polyoxethylene stearate, or condensation products of ethylene oxide with long chain aliphatic alcohols, for example, heptadecaethyleneoxycetanol, or condensation products of ethylene oxide with partial esters derived from fatty acids and a hexitol, for example, polyoxyethylene sorbitol monooleate, or condensation product of ethylene oxide with partial esters derived from fatty acids and hexitol anhydrides, for example polyoxyethylene sorbitan monooleate. The aqueous suspensions may also contain one or more preservatives, for example ethyl, n-propyl, or p-hydroxy benzoate, one or more coloring agents, one or more flavoring agents, and one or more sweetening agents, such as sucrose, saccharin, or sodium or calcium cyclamate.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, flavoring, and coloring agents, may also be present.

Syrups and elixirs may be formulated with sweetening agents, for example glycerol, sorbitol or sucrose. Such formulations may also contain a demulcent, a preservative and flavoring and coloring agents. The pharmaceutical compositions may be in the form of a sterile injectable preparation, for example as a sterile injectable aqueous suspension. This suspension may be formulated according to the known art using those suitable dispersing or wetting agents and suspending agents which have been mentioned above. The sterile injectable preparation may also be a sterile injectable solution or suspension in non-toxic parenterally-acceptable diluent or solvent, for example as a solution in 1,3-butanediol.

Term "therapeutically-acceptable acid addition salts", as used herein means those non-toxic therapeutically acceptable acid additional salts which do not adversely affect the pharmaceutical properties of the parent compounds. With respect to these additional salts, suitable inorganic anions included, for example, chloride, bromide, iodide, sulfate, phosphate, nitrate, and the like. Suitable organic anions include, for example, acetate, benzoate, lactate, propionate, butyrate, valerate, tartrate, maleate, fumarate, citrate, succinate, tosylate, ascorbate, nicotinate, adipate and gluconate.

The term "physiologically-acceptable carrier" as used herein means an acceptable cosmetic vehicle suitable for topical application to the skin of one or more non-toxic excipients which do not react with, or reduced the effectiveness of, the active ingredient contained therein.

The term "effective amount" means a predetermined antiviral amount of the antiviral agent which is effective against the viral organism in vivo.

The antiviral activity of the compounds of this invention may be demonstrated by biochemical, microbiological and biological procedures showing the inhibitory effect of the compounds on the replication of herpes simplex viruses, types 1 and 2 (HSV-1 and HSV-2); and other herpes viruses, for example, varicell zoster virus (VZV), Epstein-Barr virus (EBV) equne herpes virus (EHV) and pseudorabies virus (PRV).

A method for demonstrating the therapeutic effect of the compounds of this invention is the guinea pig model for cutaneous herpes simplex viral infections. When a compound of this invention, or one of its therapeutically-acceptable salts, is employed as an anti-viral agent, it is administered topically or systemically to warm-blooded animals, e.g., humans, pigs or horse, in a vehicle comprising one or more pharmaceutically-acceptable carriers, the proportion of which is determined by the solubility and chemical nature of the compound of this invention, chosen route of administration and standard biological practice. For topical administration, the compounds of this invention can be formulated in pharmaceutically-accepted vehicles containing about 0.1 to 10 percent, of the active agent. Such formulations can be in the form of a solution, cream or lotion.

For systemic administration, the compounds of this invention may be administered by either intravenous, subcutaneous or intramuscular injection, in composition with pharmaceutically-acceptable vehicles or carriers. For administration by injection, it is preferred to use the compounds of this invention in solution in a sterile aqueous vehicle which may also contain other solutes, e.g., buffers or preservatives as well as sufficient quantities of pharmaceutically-acceptable salts or of glucose to make the solution isotonic.

The dosage of the compounds of this invention will vary with the form of administration and the particular active agent chosen. Furthermore, it will vary with the particular host under treatment. Generally, treatment is initiated with small dosages substantially less than the optimum dose of the compound. Thereafter, the dosage may be increased by small increments until the optimum effect under the circumstances is reached. In general, the compounds of this invention is most desirably administered at a concentration level that will generally afford anti-virally effective results without causing any harmful or deleterious side effects.

With reference to systemic administration, the compounds of this invention may be administered at a dosage of about 10 mcg to about 1000 mcg per kilogram of body weight per day, although the aforementioned variations will occur. However, a dosage level that is in the range of from about 50 mcg to 500 mcg per kilogram of body weight per day is most desirably employed in order to achieve effective results.

Although the formulations disclosed hereinabove may be effective and relatively safe medications for treating herpes viral infections, the possible concurrent administration of these formulations with other antiviral medications or agents to obtain beneficial results is not excluded. Such other antiviral medications or agents include acyclovir and anti-viral surface active agents or antiviral interrerons.

In summary, a broad range of compounds of this invention may be effective inhibitors or cell infection by each of the several enveloped viruses.

The novel compounds of the invention also find a wide variety of other industrial uses as, inter alia, precursors for phenolic resin production, host compounds for uranium recovery particularly from waste water or sea water, host compounds for triethylamines, liquid crystals, and as complexing agents in liquid-liquid separations.

CONCLUSION

From the foregoing description, one skilled in the art can easily ascertain the essential characteristics of this invention, and without departing from the spirit and scope thereof, can make various changes and modifications of the invention to adapt it to various usages and conditions. Consequently, such changes and modifications are properly, equitably, and "intended" to be, within the full range of equivalence of the following claims.

I claim:

1. A cyclic tetramer of formaldehyde and 1-naphthol, and the derivatives or analogues of said cyclic tetramer, which comprises the general structure represented by the following formulas 2–5:

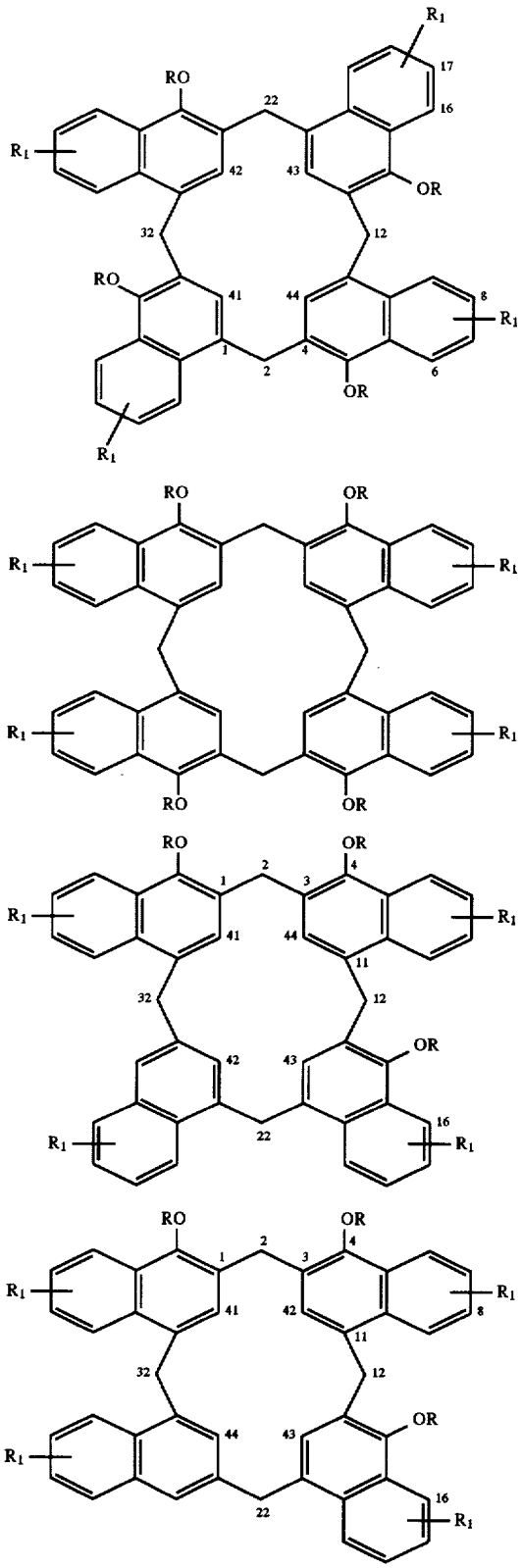

wherein:

R=H, alkyl, aromatic, CO-alkyl, and CO-aromatic; and
$R_1$=H, alkyl, aromatic, CO-alkyl, CO-aromatic, $SO_2R$ or $SO_3R$.

2. A cyclic tetramer of claim 1 with a general structure represented by the following formula 2:

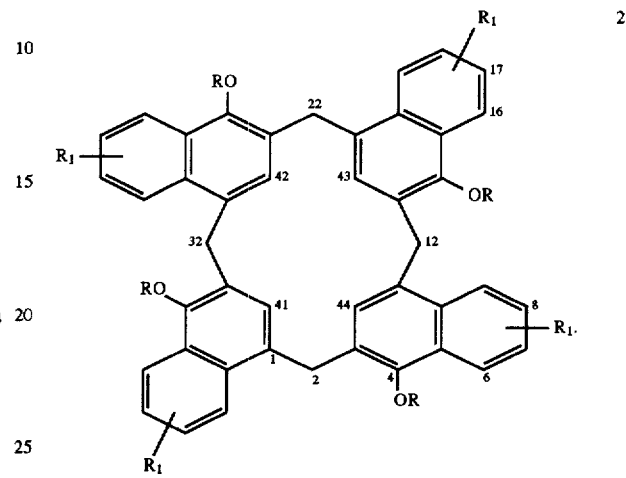

3. A cyclic tetramer of claim 1 with a general structure represented by the following formula 3:

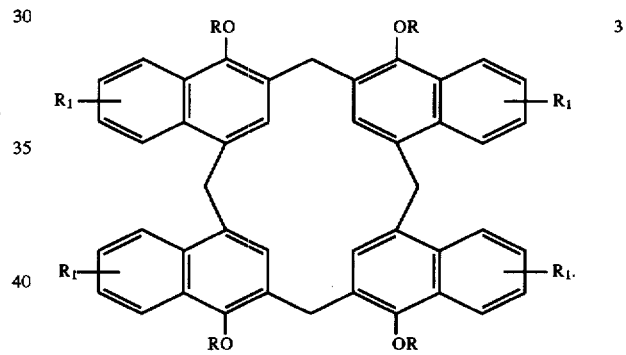

4. A cyclic tetramer of claim 1 with a general structure represented by the following formula 4:

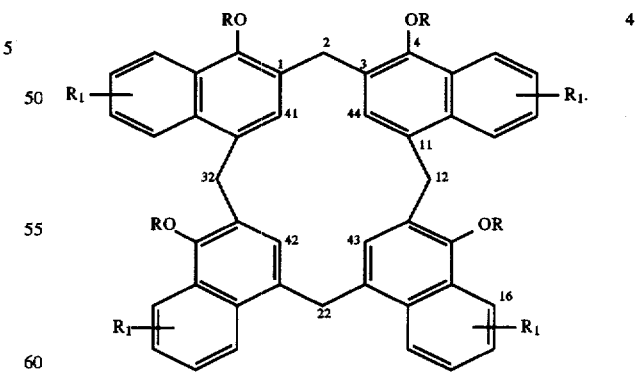

5. A cyclic tetramer of claim 1 with a general structure represented by the following formula 5:

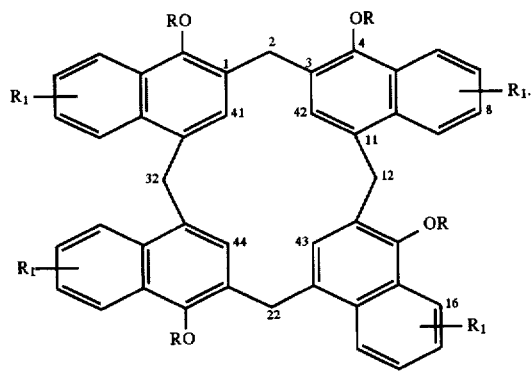

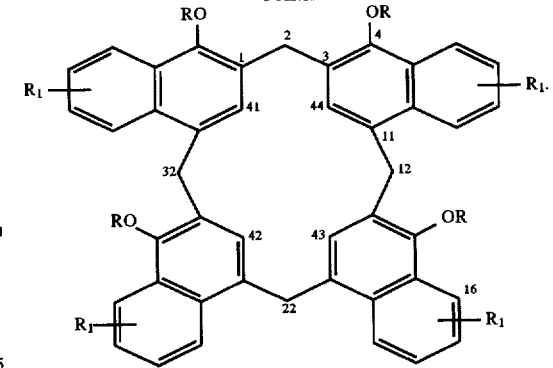

6. A method for preventing or relieving cell death or damage due to viral infections in a mammal which comprises administering, to the mammal, an effective amount of a cyclic tetramer of formaldehyde and 1-naphthol, and the derivatives or analogues of said cyclic tetramer, which comprises the general structure represented by the following formulas 2-5:

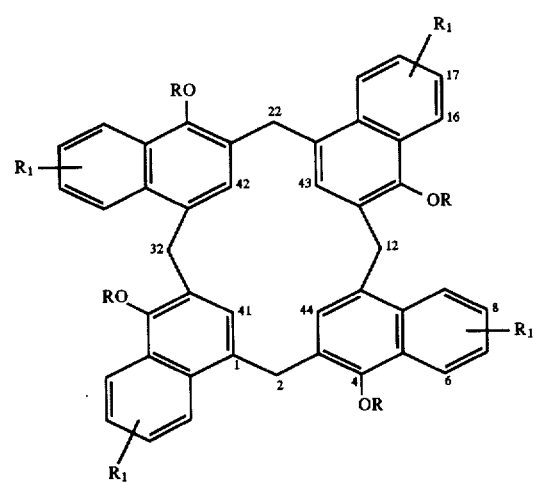

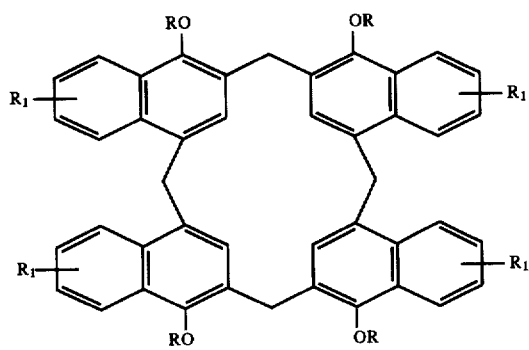

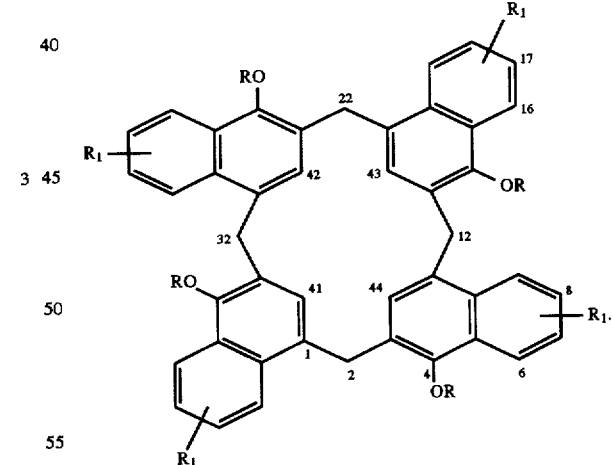

wherein:
R=H alkyl, aromatic, CO-alkyl, or CO-aromatic; and,
$R_1$=H, alkyl, aromatic, CO-alkyl, CO-aromatic, $SO_2R$, or $SO_3R$.

7. The method of claim 6 wherein said cyclic tetramer comprises a general structure represented by the following formula 2:

8. The method of claim 6 wherein said cyclic tetramer comprises a general structure represented by the following formula 3:

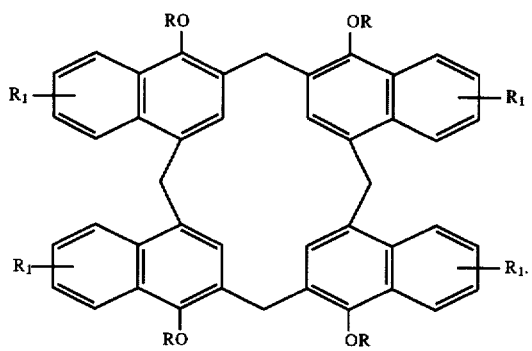

9. The method of claim 6 wherein said cyclic tetramer comprises a general structure represented by the following formula 4:

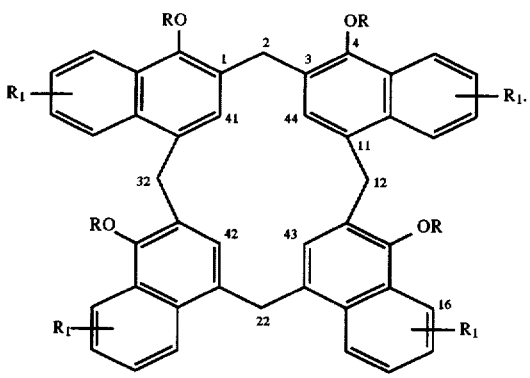

10. The method of claim 6 wherein said cyclic tetramer comprises a general structure represented by the following formula 5:

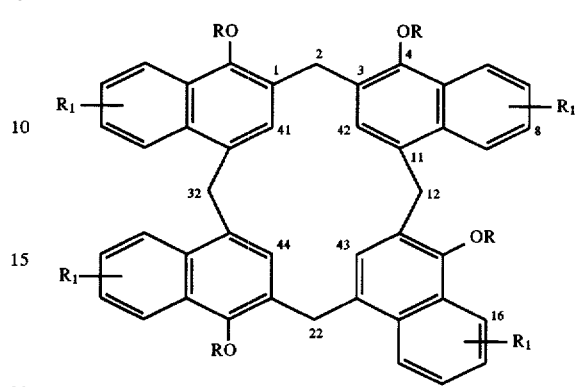

11. The method of claim 6 wherein said enveloped virus is selected from the group of virus families consisting of Orthomyxovirus, Paramyxovirus, Retrovirus and Herpesvirus.

12. The method of claim 6 wherein said enveloped virus is selected from the group consisting of HSV-1, HSV-2, Human Immunodeficiency virus (HIV), Influenza A, Influenza B, and Respiratory Syncytial Virus (RSV).

* * * * *

UNITED STATES PATENT AND TRADEMARK OFFICE
CERTIFICATE OF CORRECTION

PATENT NO. : 5,750,577
DATED : May 12, 1998
INVENTOR(S) : Paris Georghiou

It is certified that error appears in the above-indentified patent and that said Letters Patent is hereby corrected as shown below:

On the title page, at [63], after "continuation", insert -- in part --.

On the title page, in the References Cited, add the following --
5,155,132   10/92   Venuti et al .......... 514/481.

On the title page, in the References Cited, delete the third line and insert therefor -- 5,166,173   11/1992   Hwang et al ........ 514/510 --.

Column 15, line 53, delete "way" and substitute therefor --may--.

Column 15, line 57, delete "nay" and substitute therefor --may--.

Column 16, line 13, delete "were" and substitute therefor --and--.

Column 19, line 42, delete "reduced" and substitute therefor --reduce--.

Signed and Sealed this

Fourteenth Day of December, 1999

Attest:

*Attesting Officer*

Q. TODD DICKINSON

*Acting Commissioner of Patents and Trademarks*

UNITED STATES PATENT AND TRADEMARK OFFICE
CERTIFICATE OF CORRECTION

PATENT NO. : 5,750,577
DATED : May 12, 1998
INVENTOR(S) : Paris Georghiou

It is certified that error appears in the above-indentified patent and that said Letters Patent is hereby corrected as shown below:

On the title page, under OTHER PUBLICATIONS, in the first two publications cited, delete "Georghiu" and substitute therefor --Georghiou--.

Signed and Sealed this

First Day of February, 2000

Attest:

Q. TODD DICKINSON

*Attesting Officer*          *Acting Commissioner of Patents and Trademarks*